US00PP19129P2

(12) United States Plant Patent
Ui

(10) Patent No.: US PP19,129 P2
(45) Date of Patent: Aug. 19, 2008

(54) ***PETUNIA-CALIBRACHOA* PLANT NAMED 'KAKEGAWA S90'**

(50) Latin Name: *Petunia×Calibrachoa hybrida*
Varietal Denomination: Kakegawa S90

(75) Inventor: Akinobu Ui, Kakegawa (JP)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 11/703,436

(22) Filed: Feb. 7, 2007

(51) Int. Cl.
*A01H 5/00* (2006.01)

(52) U.S. Cl. ..... Plt./356

(58) Field of Classification Search ..... Plt./356
See application file for complete search history.

*Primary Examiner*—Anne Marie Grunberg
*Assistant Examiner*—Georgia Helmer
(74) *Attorney, Agent, or Firm*—Jondle & Associates, P.C.

(57) ABSTRACT

'Kakegawa S90' is a new *Petunia-Calibrachoa* hybrid particularly distinguished by having a purple flower color, medium-large flower size and a semi-creeping growth habit.

1 Drawing Sheet

Genus and species: *Petunia×Calibrachoa hybrida.*
Variety denomination: 'Kakegawa S90'.

BACKGROUND OF THE INVENTION

The present invention comprises a new and distinct cultivar of *Petunia-Calibrachoa* and hereinafter referred to by the cultivar name 'Kakegawa S90.' It is characterized by having a purple flower color, medium-large flower size and semi-creeping growth habit. The new cultivar originated from a hybridization in Kakegawa, Japan in May of 2003. The male parent was a proprietary hybrid *Calibrachoa* line named '04-62', having a deep blue flower color, medium flower size and a creeping plant habit. The female parent was a proprietary hybrid *Petunia* line named '04H-64', having a light purple flower color, medium flower size and mounding plant habit.

In May 2003, the new *Petunia-Calibrachoa* variety was developed using an intergeneric cross between a *Petunia* hybrid and a *Calibrachoa* hybrid species. After crossing the parent lines, 1,530 ovules were removed from flowers on the female parent and cultured by standard ovule culture techniques. In December 2003, 12 intergeneric hybrid plantlets were transplanted to soilless media for greenhouse culture and acclimization.

In March 2004, 10 plants out of 12 hybrid lines were vegetatively propagated to produce rooted cuttings. In April 2004, the 10 plants were transplanted to an open field and evaluated for flower color and plant growth habit through July. In August 2004, 'Kakegawa S90' which has a medium-large flower, purple color and semi-creeping plant growth habit was selected and vegetatively propagated.

In September 2004, 10 cuttings were evaluated in an open field through November 2004. The selection subsequently was named 'Kakegawa S90' and found to retain its distinctive characteristics through successive asexual propagations.

SUMMARY OF THE INVENTION

The following are the most outstanding and distinguishing characteristics of this new cultivar when grown under normal horticultural practices in Kakagawa, Japan.

1. Purple flower color;
2. Medium to large size flowers; and
3. A semi-creeping plant growth habit.

DESCRIPTION OF PHOTOGRAPHS

This new *Petunia-Calibrachoa* plant is illustrated by the accompanying photographs of an 8-month-old plant which show the plant's form, foliage and flowers. The colors shown are as true as can be reasonably obtained by conventional photographic procedures.

DESCRIPTION OF THE NEW CULTIVAR

Figure 1:
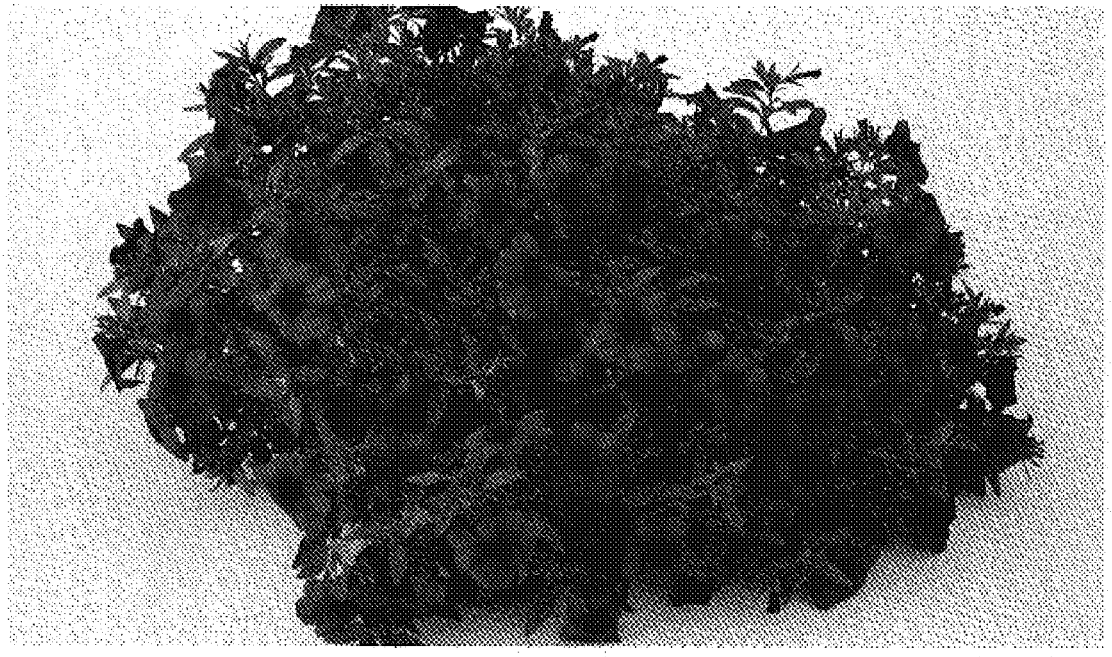
FIG. 1 shows overall plant habit.
Figure 2:
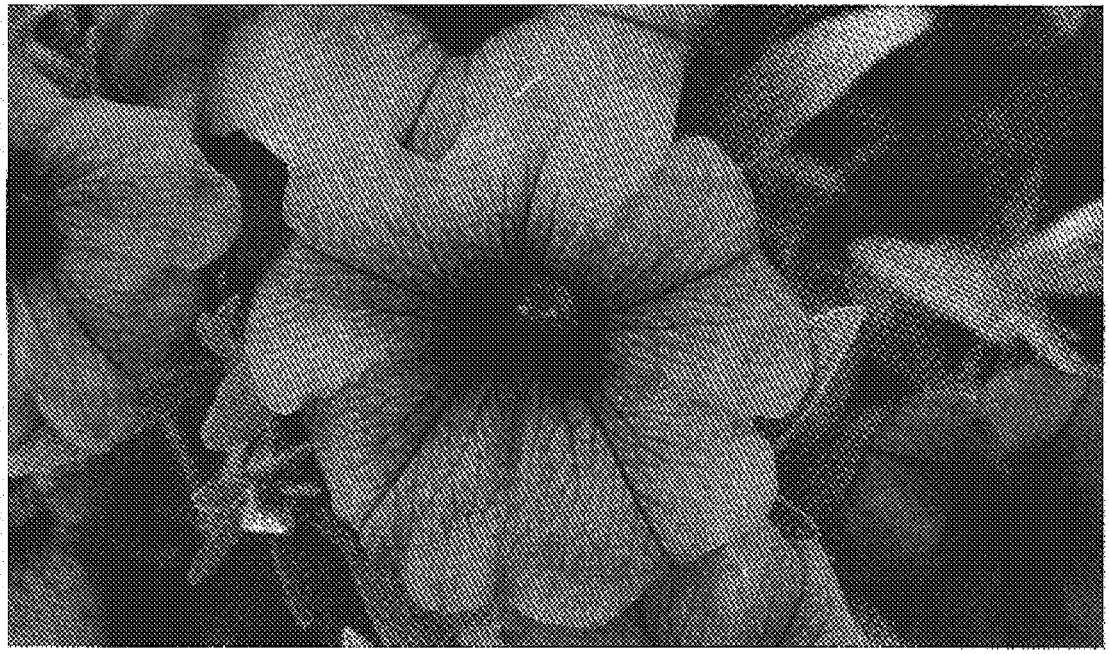
FIG. 2 shows the mature flowers.

The following detailed description sets forth the distinctive characteristics of 'Kakegawa S90'. The data which define these characteristics were collected from asexual reproductions carried out in Salinas, Calif. The detailed description was taken from plants grown under greenhouse conditions for approximately 8 months from transplanting of rooted cuttings. Color references are to the R.H.S. Colour Chart of The Royal Horticultural Society of London (RHS), $4^{th}$ Edition.

DETAILED BOTANICAL DESCRIPTION

Classification:
- *Family.*—Solanaceae.
- *Species.*—*Petunia-Calibrachoa* hybrid.
- *Common name.*—*Petunia-Calibrachoa.*

Parentage:
- *Male.*—Hybrid proprietary *Calibrachoa* breeding line '04-62'.
- *Female.*—Hybrid proprietary *Petunia* breeding line '04H-64'.

Plant description:
- *Life cycle.*—Tender perennial.
- *Form.*—Decumbent, branching.
- *Habit.*—Spreading.
- *Height.*—18.0 cm to 20.0 cm.
- *Spread.*—90.0 cm to 100.0 cm.

Propagation:
*Type cuttings.*—Vegetative cuttings.
*Time to produce a rooted cutting.*—4 weeks.
*Time to bloom from propagation.*—8 to 10 weeks.

Environmental conditions for plant growth: The terminal 1.0 to 1.5 inches of an actively growing stem was excised. The vegetative cuttings were propagated in four weeks. The base of the cuttings was dipped for 1 to 2 seconds in a 1:9 solution of DIP 'N GROW (1 solution:9 water) root inducing solution immediately prior to sticking into the cell trays. Cuttings were stuck into plastic cell trays having 98 cells, and containing a moistened peat moss-based growing medium. For the first week, the cuttings were misted with water from overhead for 20 seconds, one time per hour. For the second week, the cutting were misted one time every 2 hours for 10 seconds. After that time, the cuttings were misted occasionally until sufficient roots were formed. Rooted cuttings were transplanted and grown in 20 cm diameter plastic pots in a glass greenhouse located in Salinas, Calif. Pots contained a peat moss-based growing medium. Soluble fertilizer containing 20% nitrogen, 10% phosphorus and 20% potassium was applied once a day or every other day by overhead irrigation. Pots were top-dressed with a dry, slow release fertilizer containing 20% nitrogen, 10% phosphorus and 18% potassium. The typical average air temperature was 24° C.

Stems:
*Stem color.*—RHS 144B (Yellow-green).
*Anthocyanin color.*—Slightly present on stems, RHS N77C (Purple).
*Pubescence.*—Medium.
*Pubescence color.*—RHS N155A (White).
*Stem description.*—Round.
*Stem diameter.*—2.0 cm to 3.0 cm.
*Stem length.*—Approximately 2.0 cm from soil line to first node.
*Internode length.*—3.0 cm to 5.0 cm.

Leaves:
*Arrangement.*—Alternate.
*Shape.*—Elliptical.
*Apex.*—Obtuse.
*Base.*—Attenuate.
*Margin.*—Entire.
*Surface.*—Dull.
*Surface pubescence.*—Slight.
*Pubescence color.*—RHS N155A (white).
*Venation.*—Pinnate.
*Length.*—3.0 cm to 5.0 cm.
*Width.*—1.0 cm to 2.0 cm.
*Color.*—Upper surface: RHS 137B (Green). Lower surface: RHS 138B (Green).
*Fragrance.*—Absent.

Flowers:
*Flowering habit.*—Indeterminate.
*Flower type.*—Solitary.
*Flowering requirements.*—Will flower so long as day length is greater than 12 hours and temperature exceeds 13° C.
*Duration of flowers.*—5 days.
*Fragrance.*—Absent.
*Corolla.*—5 petals, fused.
*Corolla shape.*—The flowers are funnel shaped with five fissures and a shallow, yet slight, indentation of the petal tip at the midvein.

Flower buds:
*Surface.*—Pubescent.
*Length.*—3.0 cm.
*Diameter.*—1.0 cm.
*Shape.*—Ovate.
*Color.*—RHS 149B (Yellow-green).
*Peduncle.*—Length: 2.5 cm. Diameter: 0.5 cm.

Flower description:
*Flower depth.*—3.0 cm to 3.5 cm.
*Flower tube length.*—3.0 cm.
*Flower tube diameter.*—1.5 cm.
*Flower diameter.*—5.0 cm to 6.0 cm.
*Pedicel color.*—RHS 144B (Yellow-green).
*Calyx.*—5 sepals fused below the middle.
*Sepals.*—Shape: Elliptical. Apex: Obtuse. Sepal color: RHS 137B (Green).
*Petals.*—Shape: Spatulate. Length: 2.0 cm to 3.0 cm. Width: 1.5 cm. Apex: Truncate. Margin: Entire. Texture: Glabrous. Color: Limb color: Upper surface: RHS N74A (Red-purple) with RHS N77A (Purple) veins. Lower surface: RHS N74C (Red-purple) with RHS N77A (Purple) veins.
*Corolla tube color.*—Inner: RHS N77A (Purple) throat, inner tube is RHS 3A (Yellow) with RHS N77A (Purple) veins. Outer: RHS N77B (Purple) with RHS N77A (Purple) veins.
*Fragrance.*—Absent.

Reproductive organs:
*Stamen number.*—5, free.
*Stamen color.*—Anther color is RHS 1C (Green-yellow). Filament color: RHS 1C (Green-yellow).
*Pollen-color.*—RHS 9A (Yellow).
*Ovary.*—Superior.
*Placenta arrangement.*—Central.
*Pistil number.*—1.
*Pistil length.*—2.0 cm.
*Stigma color.*—RHS 149A (Yellow-green).
*Style length.*—1.5 cm.
*Style color.*—RHS 149C (Yellow-green).

Fruit/seed set: No fruit and seeds produced.

Disease and insect resistance: 'Kakegawa S90' has excellent resistance to rain, heat and drought. A temperature below 10° C. is not optimal. Plants are susceptible to *Botrytis,* powdery mildew, various stems and root rots, and certain viruses, like Tobacco Mosaic Virus and Impatiens Necrotic Spotted Virus. Plants can be infested with aphids, leafminer, whitefly and various *Lepitopdera.*

COMPARISON WITH PARENTAL LINES AND KNOWN CULTIVARS

In comparison with its parental lines, *Calibrachoa* 'Kakegawa S90' is a distinct variety of *Petunia-Calibrachoa* due to its medium to large flowers, purple flower color and semi-creeping growth habit. 'Kakegawa S90' is distinguished from its parents mainly by flower color and plant growth habit as shown in Table 1 below.

TABLE 1

| Characteristic | 'Kakegawa S90' | Female Parent: '04H-64' | Male Parent: '04-62' |
|---|---|---|---|
| Flower color | Purple | Light purple | Deep blue |
| Plant growth habit | Semi-creeping | Mounding | Creeping |

*Calibrachoa* 'Kakegawa S90' is a distinct variety of *Petunia-Calibrachoa* due to its purple flower color and semi-creeping growth habit. 'Kakegawa S90' is most similar to the variety 'Dancalipet' (U.S. Plant Pat. No. 16,063); however, there are differences in the petal color and plant growth habit as described in the table below (color references are to The Royal Horticultural Society Colour Chart, $4^{th}$ edition):

TABLE 2

| Characteristic | 'Kakegawa S90' | 'Dancalipet' |
|---|---|---|
| Limb color, upper surface | RHS N74A (Red-purple) with RHS N77A (Purple) veins | RHS 74A (Red-purple) |
| Limb color, lower surface | RHS N74C (Red-purple) with RHS N77A (Purple) veins | RHS 75A (Purple) |
| Plant growth habit | Semi-creeping | Compact |

We claim:

1. A new and distinct cultivar of *Petunia-Calibrachoa* hybrid plant as shown and described herein.

* * * * *